(12) United States Patent
Miyazaki et al.

(10) Patent No.: US 6,295,126 B1
(45) Date of Patent: Sep. 25, 2001

(54) INSPECTION APPARATUS FOR FOREIGN MATTER AND PATTERN DEFECT

(75) Inventors: Yoko Miyazaki; Toshiaki Mugibayashi, both of Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/532,039

(22) Filed: Mar. 21, 2000

(30) Foreign Application Priority Data

Oct. 19, 1999 (JP) .................................................. 11-296581

(51) Int. Cl.$^7$ ...................................................... G01N 21/00
(52) U.S. Cl. ...................................... 356/237.5; 356/237.4
(58) Field of Search ............................... 356/237.1, 237.2, 356/237.3, 237.4, 237.5, 239.7, 239.8, 394; 700/110, 109; 702/35; 714/724, 745; 250/559.41, 559.42, 559, 45

(56) References Cited

U.S. PATENT DOCUMENTS

| | | | |
|---|---|---|---|
| 4,449,818 | * 5/1984 | Yamaguchi et al. | 356/237 |
| 5,801,965 | * 9/1998 | Takagi et al. | 382/149 |
| 5,923,554 | * 7/1999 | Nakata | 356/237.5 |
| 5,991,699 | * 11/1999 | Kulkarni et al. | 702/83 |
| 6,002,989 | * 12/1999 | Shiba et al. | 702/84 |
| 6,016,562 | 1/2000 | Miyazaki et al. | |
| 6,031,607 | 2/2000 | Miyazaki | |
| 6,118,525 | * 9/2000 | Fossey et al. | 356/237.2 |

FOREIGN PATENT DOCUMENTS

| | | |
|---|---|---|
| 8-285782 | 11/1996 | (JP) . |
| 11-51622 | 2/1999 | (JP) . |

* cited by examiner

*Primary Examiner*—Hoa Q. Pham
(74) *Attorney, Agent, or Firm*—Oblon, Spivak, McClelland, Maier & Neustadt, P.C.

(57) ABSTRACT

An inspection apparatus for foreign matter and pattern defects includes an optical portion (D) and an analyzer (AN). The optical portion (D) includes a microscope illumination optical system (D1) for detecting the surface of a semiconductor wafer (2) in the form of a piece of first surface information by using microscope illumination, and a laser scattering type optical system (D2) for detecting scattered laser light from the semiconductor wafer by using laser light to detect the surface of the semiconductor wafer (2) in the form of a piece of second surface information. The analyzer (AN) detects a plurality of pieces of defect information from the piece of first surface information and the piece of second surface information to categorize the plurality of pieces of defect information into three modes: a first mode containing pieces of defect information represented only in the piece of first surface information, a second mode containing pieces of defect information represented only in the piece of second surface information, and a third mode containing pieces of defect information represented in both the piece of first surface information and the piece of second surface information. The inspection apparatus can easily distinguish the types of foreign matter and defects from each other.

5 Claims, 9 Drawing Sheets

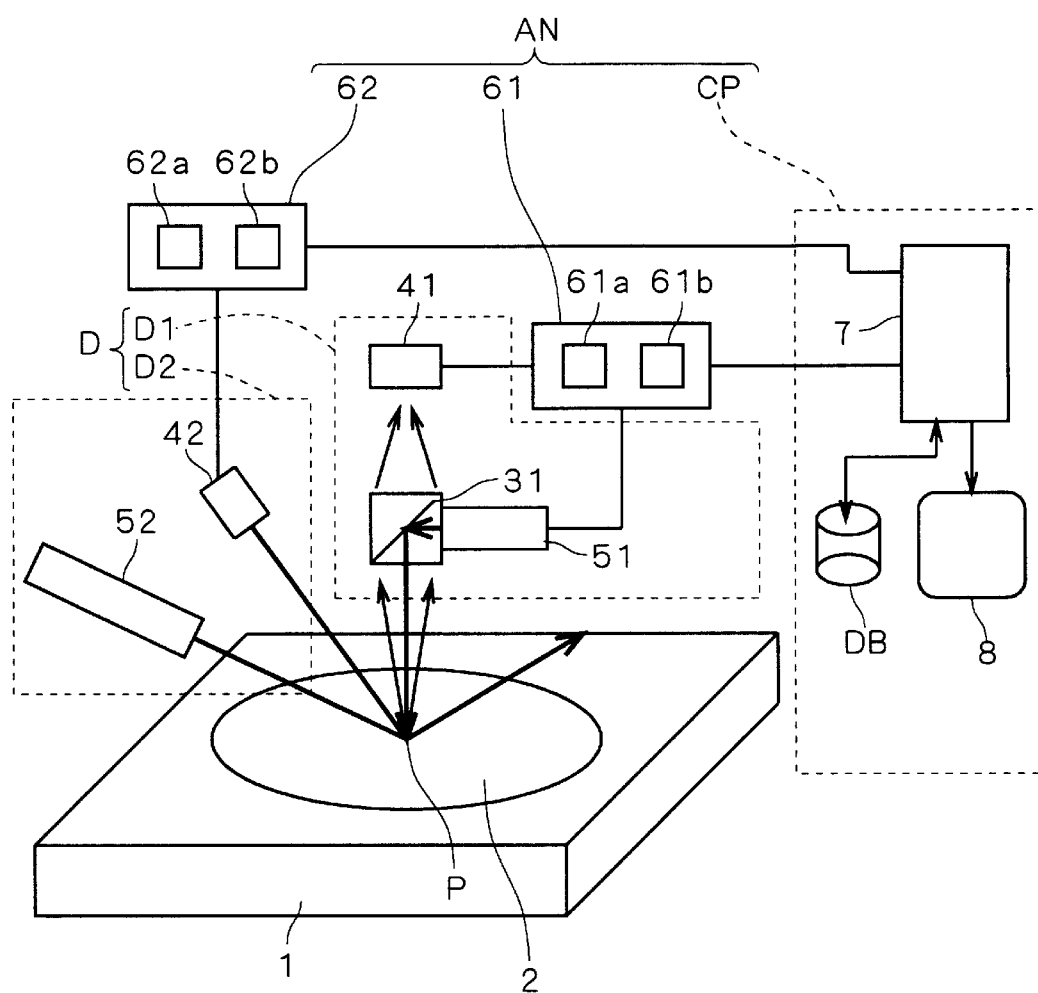
F I G . 1

| DEFECT INFORMATION | | | | | | | |
|---|---|---|---|---|---|---|---|
| DEFECT NUMBER | IMAGE DATA | OPTICAL SYSTEM | HORIZONTAL DIMENSION | VERTICAL DIMENSION | AREA | LIGHT INTENSITY | COORDINATE MODE |

FIG. 6

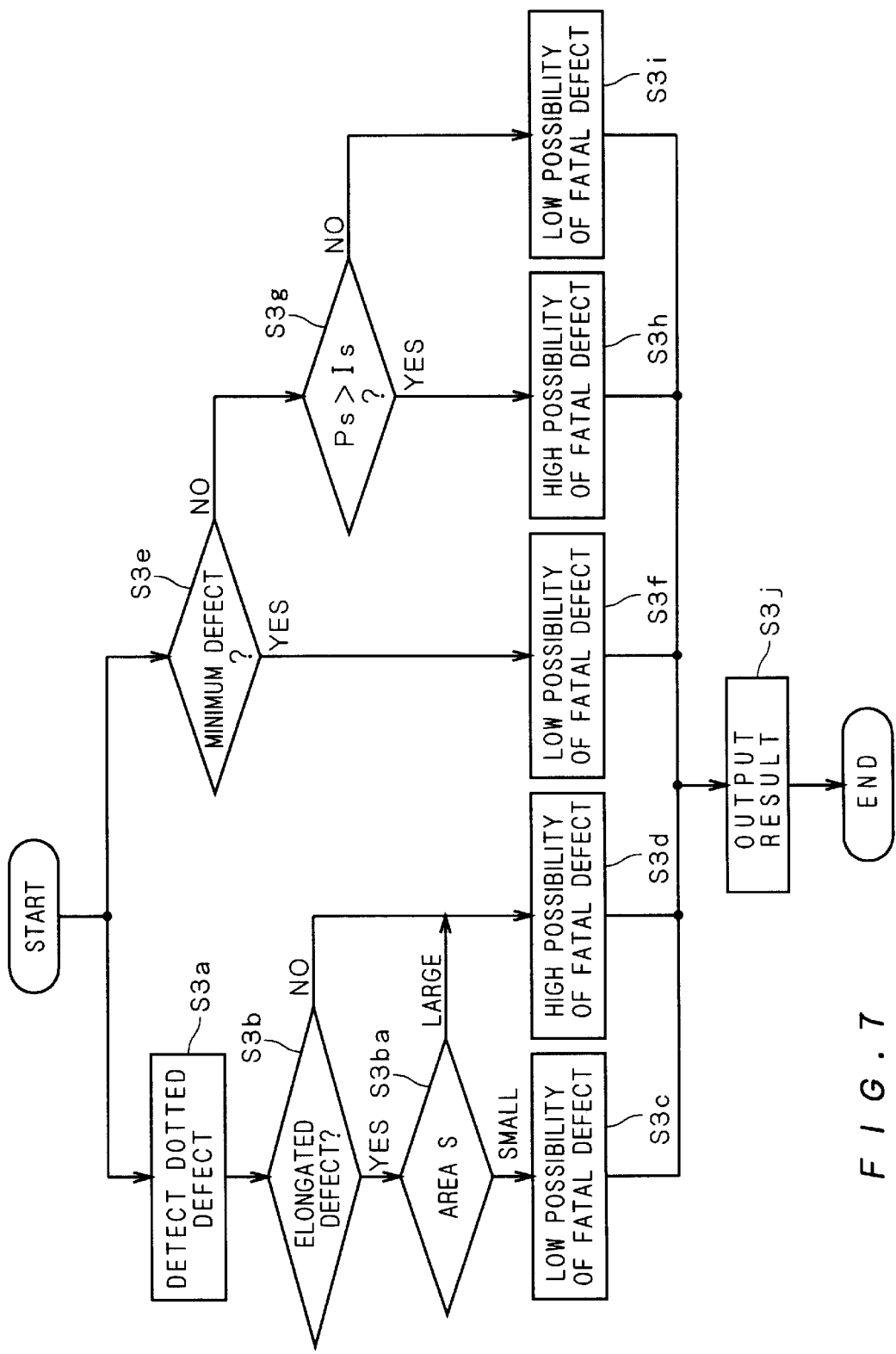
F I G . 7

<PRIOR ART>

INSPECTION APPARATUS FOR FOREIGN MATTER AND PATTERN DEFECT

BACKGROUND OF THE INVENTION

1. Field of the Invention

The present invention relates to an inspection apparatus for foreign matter and pattern defects which is used in the process of manufacturing semiconductor devices.

2. Description of the Background Art

FIG. 12 is a perspective view of a prior art inspection apparatus for foreign matter and pattern defects which is disclosed in Japanese Patent Application Laid-Open No. P11-51622A (1999).

A foreign matter inspection apparatus 10P comprises an inspection illumination device 20P for directing inspection light (laser light) 21P angularly toward a wafer 1P, and a scattered light detector 34P for detecting resultant scattered light 31P from the wafer 1P under dark field illumination, thereby determining the coordinate position of foreign matter 5P. The foreign matter inspection apparatus 10P further comprises a reflection type illumination device 40P and an image pickup device 45P. The image pickup device 45P photographs the coordinate position of the foreign matter 5P determined by a foreign matter judgement device 35P based on the detection of the scattered light detector 34P under bright field illumination provided by the reflection type illumination device 40P. The foreign matter inspection apparatus 10P extracts a foreign matter image, based on the photograph, and then specifies the size, shape, color, and property of the foreign matter, based on the extracted foreign matter image.

In FIG. 12, the reference character 2P designates a first main surface; 3P designates an orientation flat; 4P designates a pellet; 11P designates a stage device; 12P designates an XY table; 13P designates a θ table; 14P designates a controller; 22P designates a laser light irradiating device; 23P designates a condensing lens; 30P designates a scattered light detecting device; 32P designates an objective lens; 33P designates a relay lens; 41P designates white light; 42P designates a white light irradiating device; 43P designates a half mirror; 44P designates a lens; 46P designates an image processor; 47P designates a comparator; 48P designates a verifier; and 49P designates a classifier.

Foreign matter and defects are of a variety of types. For example, some foreign matter affects yields, and some foreign matter does not affect yields. Some objects look like foreign matter or defects, but actually are, for example, grain patterns such as an elongated grain boundary of an aluminum film and scratches resulting from a chemical-mechanical polishing (CMP) process.

However, the use of the image pickup device 45P for inspection for foreign matter and defects sometimes requires very long time. First, the image pickup device 45P performs focusing and magnifying actions to photograph the surface of the wafer 1P, thereby detecting surface information (a microscope image) from the wafer 1P. Next, the foreign matter inspection apparatus 10P extracts image information regarding foreign matter and defects from the microscope image photographed by the image pickup device 45P to identify foreign matter and defects. If numerous, e.g. thousands of to tens of thousands of, pieces of foreign matter and defects are detected, the above described operations require quite long time and impractical, and it is very difficult to grasp an overview of all of the foreign matter and defects within a predetermined length of time. Additionally, the microscope image is an image of the wafer 1P as viewed from above and shows only the plan configuration of the foreign matter and defects. This makes it difficult to judge whether or not the identified foreign matter and defects affect the yields.

Another method of identifying the foreign matter and defects on the wafer surface uses laser light. Laser light directed onto the wafer and scattered therefrom is detected for detection of surface information from the wafer. This method does not require the focusing and magnifying actions to detect the surface information from the wafer accordingly more quickly than the technique employing the image pickup device 45P. This shortens the time required for inspection for the foreign matter and defects. However, this method is disadvantageous in that the light scattered from a pattern defect, a fine foreign particle and a scratch-type defect is low in intensity, resulting in decreased sensitivity of detection of these defects or, in some cases, failure to detect these defects.

As described above, the method employing the microscope and the method employing the laser light have both advantages and disadvantages and present great difficulties in effectively distinguishing the above-mentioned types of foreign matter and defects from each other, based on the wafer surface information.

SUMMARY OF THE INVENTION

According to a first aspect of the present invention, an apparatus for inspecting a semiconductor wafer surface for defects and foreign matter comprises: an optical portion including a microscope illumination optical system for acquiring an image of the semiconductor wafer surface by using microscope illumination to detect the semiconductor wafer surface in the form of a piece of first surface information, and a laser scattering type optical system for detecting scattered laser light from the semiconductor wafer surface by using laser light to detect the semiconductor wafer surface in the form of a piece of second surface information; and an analyzer for detecting a plurality of pieces of defect/foreign matter information from the piece of first surface information and the piece of second surface information to categorize the plurality of pieces of defect/foreign matter information into three modes comprised of a first mode containing pieces of defect/foreign matter information represented only in the piece of first surface information, a second mode containing pieces of defect/foreign matter information represented only in the piece of second surface information, and a third mode containing pieces of defect/foreign matter information represented in both the piece of first surface information and the piece of second surface information.

Preferably, according to a second aspect of the present invention, in the apparatus of the first aspect, the analyzer further categorizes the pieces of defect/foreign matter information contained in the third mode into three modes comprised of a fourth mode containing pieces of defect/foreign matter information in which a first defect/foreign matter size represented in the piece of second surface information is greater than a second defect/foreign matter size represented in the piece of first surface information, a fifth mode containing pieces of defect/foreign matter information in which the first defect/foreign matter size is approximately equal to the second defect/foreign matter size, and a sixth mode containing pieces of defect/foreign matter information in which the first defect/foreign matter size is smaller than the second defect/foreign matter size.

Preferably, according to a third aspect of the present invention, in the apparatus of the second aspect, the analyzer counts the number of pieces of defect/foreign matter information contained in the fourth mode.

According to a fourth aspect of the present invention, an apparatus for inspecting a semiconductor wafer surface for defects and foreign matter comprises: an optical portion for detecting the semiconductor wafer surface in the form of a piece of surface information; and an analyzer for detecting a plurality of pieces of defect/foreign matter information each including a horizontal dimension, a vertical dimension and the area of a defect/foreign matter from the piece of surface information to calculate a predetermined elongation factor indicating a degree to which each defect/foreign matter is elongate from the horizontal dimension, the vertical dimension and the area thereof.

Preferably, according to a fifth aspect of the present invention, in the apparatus of the fourth aspect, the elongation factor equals the area divided by the sum of the horizontal dimension squared and the vertical dimension squared; and the analyzer discriminates pieces of defect/foreign matter information including the elongation factor of less than 0.5 and pieces of defect/foreign matter information including the area of less than a predetermined value from other pieces of defect/foreign matter information.

Preferably, according to a sixth aspect of the present invention, in the apparatus of the fourth aspect, the analyzer excludes pieces of defect/foreign matter information detected by the analyzer and including the elongation factor of less than a predetermined value from subjects of analysis when the semiconductor wafer surface includes a metal film.

Preferably, according to a seventh aspect of the present invention, in the apparatus of the first aspect, the optical portion and the analyzer operate in parallel with each other.

Preferably, according to an eighth aspect of the present invention, in the apparatus of the fifth aspect, the analyzer excludes pieces of defect/foreign matter information detected by the analyzer and including the elongation factor of less than a predetermined value from subjects of analysis when the semiconductor wafer surface includes a metal film.

Preferably, according to a ninth aspect of the present invention, in the apparatus of the fourth aspect, the optical portion and the analyzer operate in parallel with each other.

In accordance with the first aspect of the present invention, since defects/foreign matter is detected by the microscope illumination optical system and/or the laser scattering type optical system, the analyzer can easily categorize all pieces of defect/foreign matter information into the three modes. These modes are used to easily control the quality, process and yield of products.

In accordance with the second aspect of the present invention, the difference in property between the illumination optical system and the laser optical system is utilized to assign the defect/foreign matter information having a high possibility of affecting the yield to the fourth mode, the defect/foreign matter information having a medium-level possibility thereof to the fifth mode, and the defect/foreign matter information having a low possibility thereof to the sixth mode, for example.

In accordance with the third aspect of the present invention, the yield is accurately predicted from the number of pieces of defect/foreign matter information counted by the analyzer.

In accordance with the fourth aspect of the present invention, whether or not the possibility that a defect/foreign matter affects the yield is low is found from the elongation factor of the defect/foreign matter. Thus, the yield is accurately predicted.

In accordance with the fifth aspect of the present invention, elongated defects/foreign matter having a low possibility of affecting the yield or extremely small defects/foreign matter is found. Thus, the yield is more accurately predicted.

In accordance with the sixth aspect of the present invention, even if a large number of grain patterns might be detected as defects/foreign matter when the semiconductor wafer surface includes a metal film, the exclusion of the pieces of defect/foreign matter information including the elongation factor of less than the predetermined value from the subjects of analysis accomplishes accordingly accurate analysis.

In accordance with the seventh aspect of the present invention, the result of the analysis of the semiconductor wafer is obtained immediately after the completion of all operations of the optical portion upon the semiconductor wafer.

In accordance with the eighth aspect of the present invention, even if a large number of grain patterns might be detected as defects/foreign matter when the semiconductor wafer surface includes a metal film, the exclusion of the pieces of defect/foreign matter information including the elongation factor of less than the predetermined value from the subjects of analysis accomplishes accordingly accurate analysis.

In accordance with the ninth aspect of the present invention, the result of the analysis of the semiconductor wafer is obtained immediately after the completion of all operations of the optical portion upon the semiconductor wafer.

It is therefore an object of the present invention to provide an inspection apparatus for foreign matter and pattern defects which is capable of easily distinguishing the types of foreign matter and defects from each other.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a schematic view of an inspection apparatus for foreign matter and pattern defects according to a first preferred embodiment of the present invention;

FIG. 6 shows a data structure of an example of defect information according to the first preferred embodiment;

FIG. 7 is a flowchart showing the operation of the inspection apparatus for foreign matter and pattern defects according to a third preferred embodiment of the present invention;

DESCRIPTION OF THE PREFERRED EMBODIMENTS

First Preferred Embodiment

Figure 2:
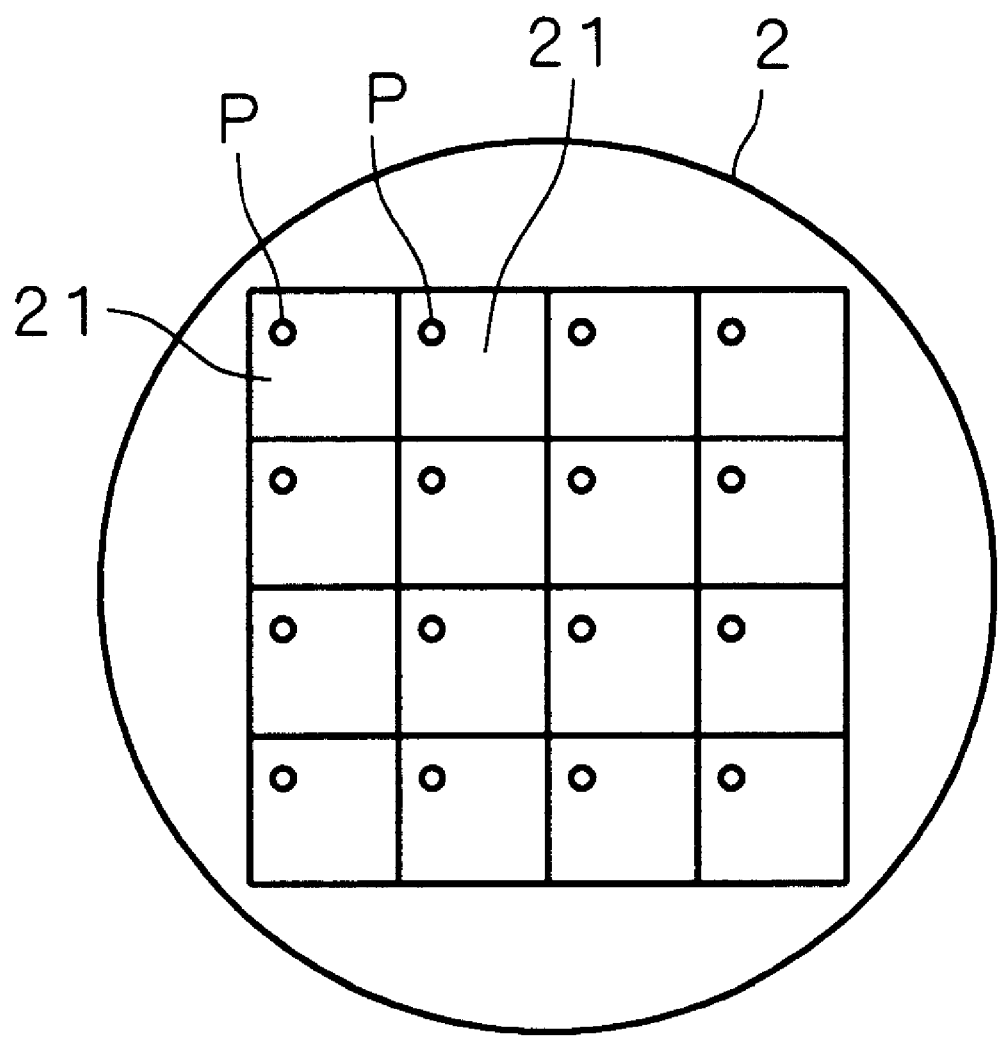
FIG. 2 is a plan view of an example of semiconductor wafers.

A first preferred embodiment according to the present invention will now be described. FIG. 1 is a schematic view of an inspection apparatus for foreign matter and pattern defects according to the first preferred embodiment of the present invention. The inspection apparatus is an apparatus for inspecting a semiconductor wafer surface for foreign matter and defects (pattern defects and the like).

The inspection apparatus according to the first preferred embodiment comprises an inspection stage (wafer stage) 1, an optical portion D, and an analyzer AN.

The inspection stage 1 is provided to move a semiconductor wafer 2 placed thereon to a determined position.

The optical portion D comprises a microscope illumination optical system D1 and a laser scattering type optical system D2. The microscope illumination optical system D1 detects the surface of the semiconductor wafer 2 in the form of a piece of first surface information (more specifically, image information) by means of an illumination light source, and comprises a lens system 31, a detector 41, and an illumination light source 51. The laser scattering type optical system D2 detects the surface of the semiconductor wafer 2 in the form of a piece of second surface information (more specifically, the intensity of scattered laser light) by means of a laser light source, and comprises a detector 42 and a laser light source 52.

The analyzer AN comprises a signal processor 61, a signal processor 62 and a computer CP. The signal processor 61 detects foreign matter and defects (both of which are generically referred to hereinafter as defects in a broad sense; i.e., a defect in a broad sense is meant to include foreign matter) on the surface of the semiconductor wafer 2 in the form of respective pieces of first defect information from the first surface information, and comprises a surface information storage circuit 61a and a defect information processing circuit 61b. The signal processor 62 detects defects on the surface of the semiconductor wafer 2 in the form of respective pieces of second defect information from the second surface information, and comprises a surface information storage circuit 62a and a defect information processing circuit 62b. The computer CP comprehensively analyzes and outputs defects, based on the pieces of first defect information from the signal processor 61 and the pieces of second defect information from the signal processor 62, and comprises a defect judgement device 7, a display device 8, and a database DB.

The signal processor 61 and the signal processor 62 may be included in the defect judgement device 7 of the computer CP.

The operation of the inspection apparatus will be described hereinafter.

The semiconductor wafer 2 has a plurality of semiconductor integrated circuit formation regions 21, as illustrated in FIG. 2. The inspection apparatus may regard a semiconductor wafer having no patterns but only films hypothetically as having a pattern, to thereby similarly handle the semiconductor wafer.

The operation of the microscope illumination optical system D1 will be described first. The illumination light source 51 directs light toward a region P to be subjected to defect detection in a semiconductor integrated circuit formation region 21 of the semiconductor wafer 2. The lens system 31 receives light reflected from the region P of the semiconductor wafer 2 to form an image. The detector 41 detects the image-formed light from the lens system 31 in the form of the piece of first surface information (more specifically, image information) to output the piece of first surface information to the signal processor 61. The lens system 31, the detector 41 and the illumination light source 51 repeatedly perform the above-mentioned operation upon other semiconductor integrated circuit formation regions 21 to output a plurality of pieces of first surface information to the signal processor 61.

The operation of the laser scattering type optical system D2 will be described. The laser scattering type optical system D2 detects the surface of the same region P in the form of the piece of second surface information (more specifically, the intensity of scattered laser light) simultaneously with the microscope illumination optical system D1. The laser scattering type optical system D2 can extract the information about the surface of the semiconductor wafer 2 more finely than the microscope illumination optical system D1. More specifically, the laser light source 52 directs laser light onto the region P (or the vicinity of the region P) in a semiconductor integrated circuit formation region 21 of the semiconductor wafer 2. The width of the laser light is reduced to about one to several micrometers so that fine defects are extracted. The laser light source 52 causes the laser light of reduced width to scan, thereby directing the laser light of reduced width throughout the region P (or a region having the same area as the region P when directing the laser light onto the vicinity of the region P) Preferably, the laser light is directed throughout the region P for a short time so that the first defect information and the second defect information are obtained at the same time. The detector 42 receives light reflected and scattered from the region P (or the vicinity of the region P) of the semiconductor wafer 2 to detect the reflected and scattered light in the form of the piece of second surface information, outputting the piece of second surface information to the signal processor 62. The detector 42 and the laser light source 52 repeatedly perform the above-mentioned operation upon other semiconductor integrated circuit formation regions 21 to output a plurality of pieces of second surface information to the signal processor 62. The piece of second surface information outputted from the detector 42 is one-dimensional information obtained by scanning the two-dimensional region P.

In this manner, the microscope illumination optical system D1 and the laser scattering type optical system D2 which differ in type from each other are used to detect defects in the same region P on the wafer surface in the form of the piece of first surface information and the piece of second surface information, respectively.

Next, the operation of the signal processor 61 will be described. The surface information storage circuit 61a of the signal processor 61 receives and stores therein the plurality of pieces of first surface information. The defect information processing circuit 61b determines differences between the plurality of pieces of first surface information stored in the surface information storage circuit 61a to extract surface information (image information) which is likely to be associated with defects from the first surface information. The defect information processing circuit 61b compares the surface information which is likely to be associated with defects with a predetermined defect size to extract defects in the form of respective pieces of first defect information from the first surface information. The defect size is suitably set by a user based on his empirical judgement in accordance with device design rules or the sensitivity setting of the inspection apparatus or automatically set by the inspection apparatus based on a discriminant.

The operation of the signal processor 62 will be described. The signal processor 62 converts the one-dimensional second surface information into two-dimensional second surface information (image information corresponding to a pixel array herein). The surface information storage circuit 62a receives and stores therein the plurality of pieces of two-dimensional second surface information. The defect information processing circuit 62b determines differences between the plurality of pieces of second surface information stored in the surface information storage circuit 62a to extract surface information which is likely to be associated with defects from the second surface information. The defect information processing circuit 62b compares the surface information which is likely to be associated with defects with a predetermined defect size to extract defects in the form of respective pieces of second defect information from the second surface information. The defect size is suitably set by a user in accordance with device design rules or the sensitivity setting of the inspection apparatus or automatically set by the inspection apparatus based on a discriminant.

Figure 3:
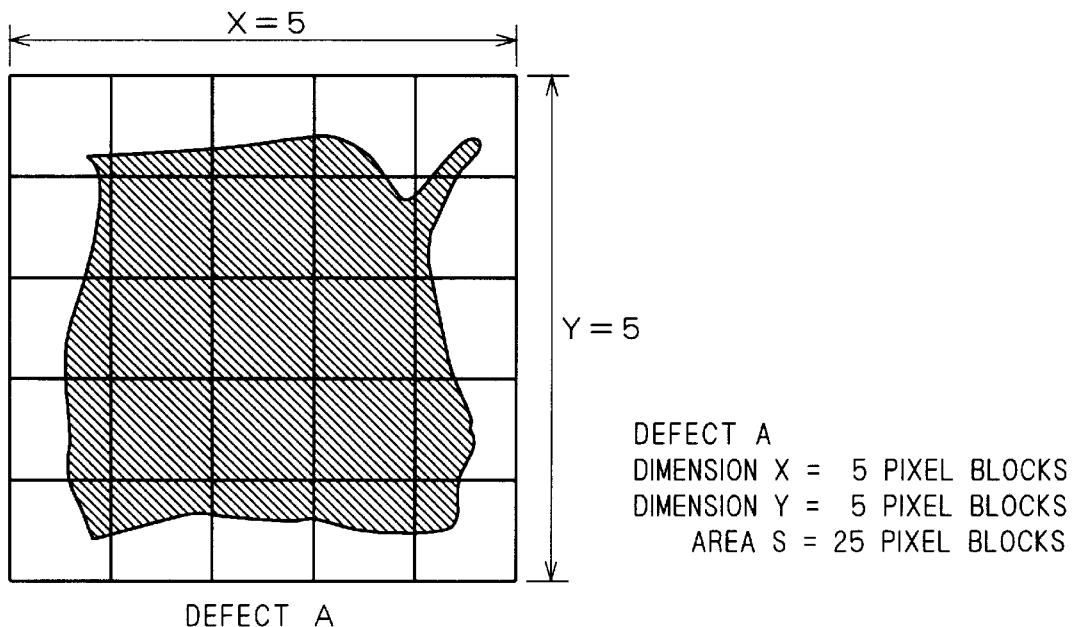
FIGS. 3 and 4 show examples of surface information according to the first preferred embodiment.
Figure 4:
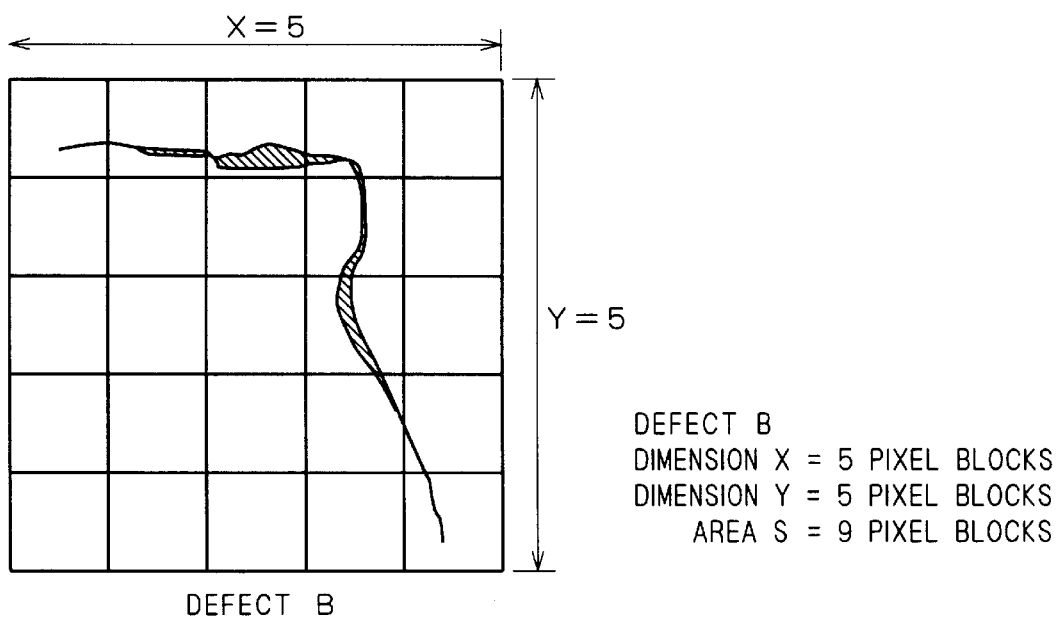

Each piece of the first and second defect information contains surface information and parameters as shown in FIGS. 3 and 4, that is, the area S, the horizontal dimension X and the vertical dimension Y of a defect. FIG. 3 shows a relatively round defect A, and FIG. 4 shows a relatively elongated defect B. The area S is the total number of pixel blocks in which a defect is present, the dimension X is the total number of horizontally arranged pixel blocks in which the defect is present, and the dimension Y is the total number of vertically arranged pixel blocks in which the defect is present.

The defect judgement device 7 of the computer CP comprehensively analyzes defects, based on the first and second defect information.

Figure 5:
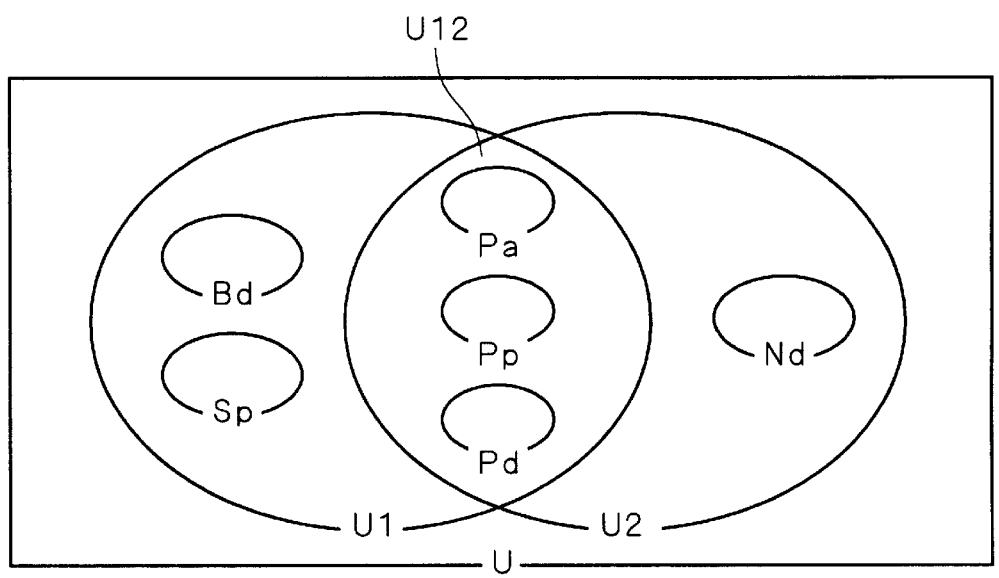
FIG. 5 is a Venn diagram showing a relationship between three modes according to the first preferred embodiment.

As above described, defects are detected by the microscope illumination optical system D1 and the laser scattering type optical system D2. Thus, the defect judgement device 7 can easily categorize a set U of defects all detected by the microscope illumination optical system D1 and the laser scattering type optical system D2 into three modes (sets) U1, U2 and U12, as shown in FIG. 5.

Figure 12:
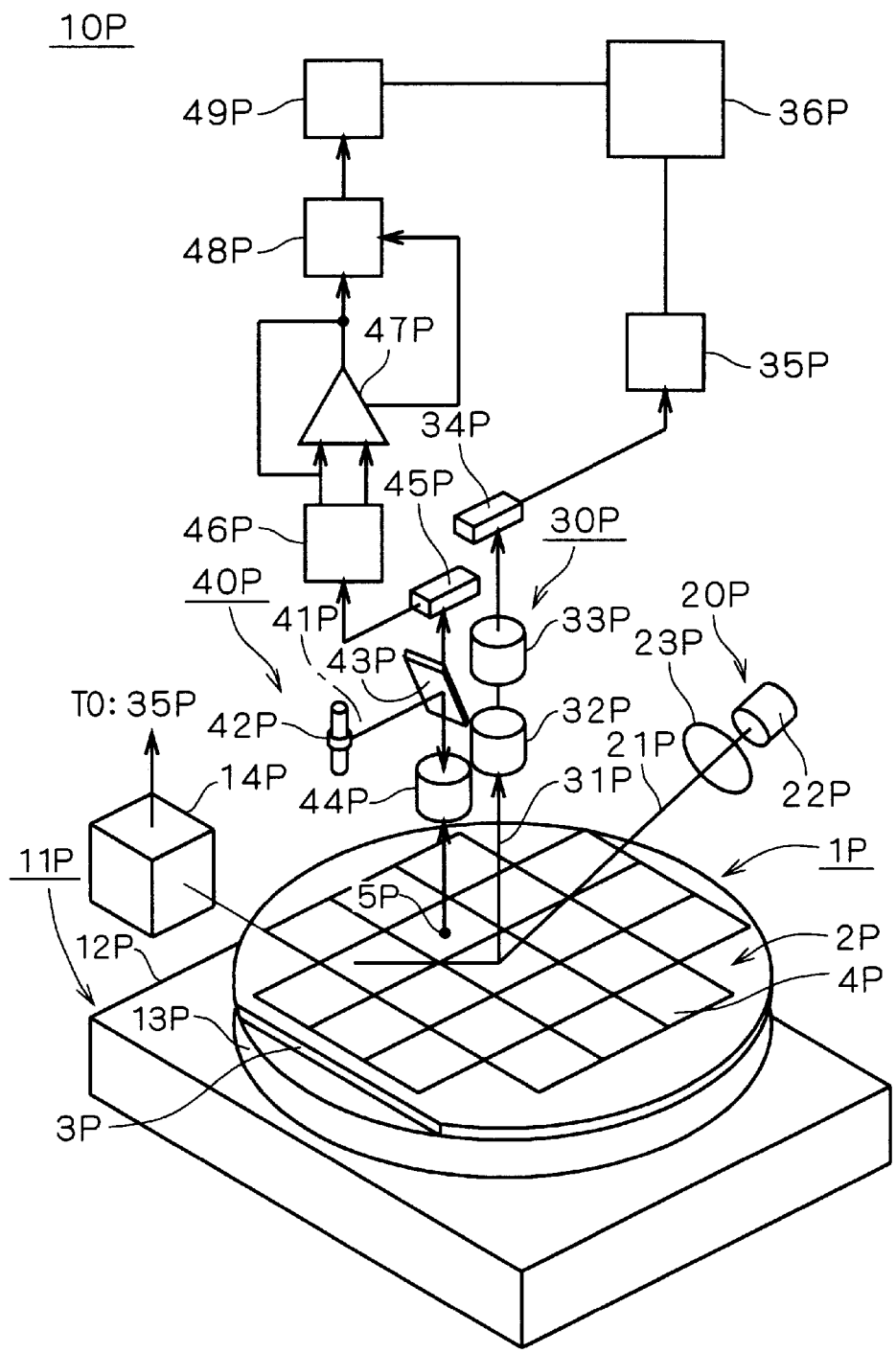
FIG. 12 is a schematic view of a prior art inspection apparatus for foreign matter and pattern defects.

In the inspection apparatus shown in FIG. 12, the scattered light detector 34P and the image pickup device 45P do not simultaneously operate, but the scattered light detector 34P specifies the coordinate position of the foreign matter 5P and a host computer 36P or the like performs the conventional inspection for foreign matter and defects, following which the image pickup device 45P detects (photographs) the foreign matter 5P at the coordinate position. This requires much time for inspection. In the inspection apparatus of the first preferred embodiment, on the other hand, the microscope illumination optical system D1 and the laser scattering type optical system D2 detect the same defect at the same time, as above discussed, to reduce the time required for inspection.

The mode U1 is a set of pieces of defect information represented only in the first surface information, the mode U2 is a set of pieces of defect information represented only in the second surface information, and the mode U12 is a set of pieces of defect information represented in both the first and second surface information.

Preferably, the defect judgement device 7 further categorizes the modes U1, U2 and U12 into sub-modes.

In the instance shown in FIG. 5, the mode U1 contains an intra-film defect mode Bd and a stain-type defect mode Sp. The mode U2 contains a defect candidate mode Nd. The mode U12 contains a surface foreign matter deposition mode Pa, a foreign matter deposited pattern defect mode Pp, and a pattern defect mode Pd.

The intra-film defect mode Bd and the stain-type defect mode Sp contained in the mode U1 are described first. The microscope illumination optical system D1 detects not only defects on the film of interest but also a defect in the film (intra-film defect) and a slightly differently colored stain (stain-type defect). The defect judgement device 7 judges that, among the defects included in the mode U1, defects of a size not greater than a predetermined value (e.g., about 3 μm) are included in the intra-film defect mode Bd and other defects are included in the stain-type defect mode Sp.

Next, the surface foreign matter deposition mode Pa, the foreign matter deposited pattern defect mode Pp, and the pattern defect mode Pd contained in the mode U12 will be described. The image detected by the microscope illumination optical system D1 is an image of the semiconductor wafer 2 as viewed from above and therefore has dimensions equaling the actual dimensions. However, the image detected by the laser scattering type optical system D2 appears such that a pattern image is elongated since the laser light source 52 directs light angularly, and the image of some pattern shapes (e.g., a tall pattern) has dimensions greater than the actual dimensions. The taller the pattern having a defect, the higher the possibility that the defect becomes a fatal defect to the pattern. Utilizing this characteristic, the defect judgement device 7 makes a comparison between the size Is of the defect (the dimension X, the dimension Y or the area S of the defect) given from the first surface information and the size Ps of the defect (the dimension X, the dimension Y or the area S of the defect) given from the second surface information. The defect judgement device 7 judges that the defect is included in the surface foreign matter deposition mode Pa if the size Ps is greater than the size Is, in the foreign matter deposited pattern defect mode Pp if the size Ps is approximately equal to the size Is, and in the pattern defect mode Pd if the size Ps is smaller than the size Is. This assigns a defect having a high possibility of becoming the fatal detect to the surface foreign matter deposition mode Pa, a defect having a medium-level possibility thereof to the foreign matter deposited pattern defect mode Pp, and a defect having a low possibility thereof to the pattern defect mode Pd.

The defect candidate mode Nd contained in the mode U2 will be described. The defect candidate mode Nd contains defects which are detected by the laser scattering type optical system D2 but are not included in the mode U12. Thus, the defect judgement device 7 judges that defects which are included in neither the mode U1 nor the mode U12 among the multiplicity of detected defects in the set U are included in the defect candidate mode Nd. The detector 42 of the laser scattering type optical system D2, when increased in detection sensitivity to the reflected and scattered light, detects mere roughness of the surface of the semiconductor wafer 2 and mere irregular edge shapes of the pattern formed on the surface of the semiconductor wafer 2 as defects, as well as the intended defects. Such defects are included in the defect candidate mode Nd.

Thus, the detection of defects using the microscope illumination optical system D1 and the laser scattering type optical system D2 allows the defects to be categorized into the various modes. These modes are used to easily control the quality, process and yield of products.

The first preferred embodiment not only combines the microscope illumination optical system D1 and the laser scattering type optical system D2 simply together but also utilizes well a difference in property between the microscope illumination optical system D1 and the laser scattering type optical system D2. For example, the difference in size between the image detected by the microscope illumination optical system D1 and the image detected by the laser scattering type optical system D2 is used as above described to assign the defect having the high possibility of becoming the fatal detect to the surface foreign matter deposition mode Pa, the defect having the medium-level possibility thereof to the foreign matter deposited pattern defect mode Pp, and the defect having the low possibility thereof to the pattern defect mode Pd. This is not accomplished by simply combining the microscope illumination optical system D1 and the laser scattering type optical system D2. Further, the microscope illumination optical system D1 has the disadvantage of requiring much time for inspection but has the advantage of having good detection sensitivity to a recess-type defect, a stain-type defect, a short defect which establishes a short circuit between patterns, and a defect hidden in the bottom of a stepped pattern. On the other hand, the laser scattering type optical system D2 has the disadvantage of having poor detection sensitivity to these defects or failing to detect these defects because of the low intensity of the scattered light, but has the advantage of requiring short time for inspection. The microscope illumination optical system D1 and the laser scattering type optical system D2 overcome their disadvantages in a mutually complementary fashion to accomplish efficient inspection.

The optical portion D performs an operation upon regions other than the region P of the semiconductor wafer 2. During the operation of the optical portion D, the defect judgement device 7 of the computer CP comprehensively analyzes the pieces of first and second defect information from the optical portion D. Thus, the optical portion D and the computer CP operate in parallel with each other, thereby providing the result of the analysis of the semiconductor wafer 2 immediately after the completion of all operations of the optical portion D upon the semiconductor wafer 2.

The computer CP stores the analytical result such as the above-mentioned modes in the database DB, and displays on the display device 8 as required.

FIG. 6 shows an example of a piece of defect information constituting the above-mentioned analytical result of a single defect. The single piece of defect information comprises a defect number for identification of the defect, the surface information (image data) shown in FIGS. 3 and 4, the optical system that detected the defect (the microscope illumination optical system D1 or the laser scattering type optical system D2), the horizontal dimension X of the defect for each optical system, the vertical dimension Y of the defect, the area S of the defect, the intensity of the scattered laser light and the coordinates of the defect on the semiconductor wafer 2 in addition to the above-mentioned modes.

All of the multiplicity of defects on the semiconductor wafer 2 do not always become fatal defects.

For example, there is a high possibility that an extremely small defect (referred to hereinafter as a minimum defect) does not become the fatal defect. Whether or not a defect is too small to become the fatal defect is found from the area included in the defect information shown in FIG. 6. In particular, there is a low possibility that the defects in the pattern defect mode Pd (wherein Ps<Is) are the fatal defects (which will be described in detail later in a third preferred embodiment).

As described above, whether or not a defect is fatal is found from the piece of defect information regarding the defect. Therefore, the yield is accurately predicted by, for example, counting the number of pieces of defect information included in the surface foreign matter deposition mode Pa and indicating the fatal defects among the multiplicity of pieces of defect information and then determining the tendency of the number of fatal defects (by a line monitor).

Second Preferred Embodiment

The mode of defects to be judged about the possibility of becoming the fatal defect contains an elongated defect in addition to the minimum defect. Whether a defect which does not become the fatal defect is the elongated defect or not is not found only from the defect information shown in FIG. 6.

To solve the problem, the defect judgement device 7 calculates an elongation factor indicative of the degree to which a defect is elongate, and causes the defect information of FIG. 6 to contain the elongation factor. Thus, whether or not a defect becomes the fatal defect is found from the defect information.

The elongation factor may be calculated, for example, from $$Ge=S/(X^2+Y^2) \qquad (1)$$

In Expression (1), the elongation factor Ge equals the area S divided by the sum of the dimension X squared and the dimension Y squared.

The elongation factor will be described, taking the defect A of FIG. 3 and the defect B of FIG. 4 as an example. The horizontal and vertical dimensions X and Y of the defect A equal those of the defect B. The defect A of FIG. 3 wherein S=25 and X=Y=5 has an elongation factor Ge=0.5, and the defect B of FIG. 4 wherein S=9 and X=Y=5 has an elongation factor Ge=0.14. The smaller the elongation factor Ge is, the more elongated the defect is. The elongation factor Ge shows that the defect B is much more elongated than the defect A and has a very low possibility of becoming the fatal defect.

As above described, whether or not a defect is the elongated defect is found from the defect information containing the elongation factor. Accordingly, whether or not the defect is the fatal defect is accurately found from the defect information. This allows more accurate prediction of the yield.

Third Preferred Embodiment

The minimum defect and the elongated defect will be described in further detail according to a third preferred embodiment of the present invention.

FIG. 7 is a flowchart showing the operation of the inspection apparatus according to the third preferred embodiment of the present invention.

The inspection apparatus initially categorizes the detected defects into the modes (Steps S3a, S3b, S3ba, S3e, S3g), and then judges whether or not the defects categorized into the modes are the fatal defects (Steps S3c, S3d, S3f, S3h, S3i). The judgement about the minimum defects and the judgement about the elongated defects are separately described hereinafter.

(Elongated Defect)

The elongated defects include a grain pattern and a scratch known as a scratch defect.

The grain pattern is a defect, for example, like an elongated grain boundary of an aluminum film, and has a small area and an elongated linear configuration. The grain pattern is not the fatal defect.

The scratch is, for example, a small cut made in the CMP process, and has an elongated configuration and a large area. There is a high possibility that the scratch is the fatal defect.

Thus, the elongated defects detected by the microscope illumination optical system D1 and the laser scattering type optical system D2 are classified into grain patterns and scratches.

The defect judgement device 7 judges whether a defect is a small elongated defect or a large elongated defect (Step S3b). If the defect is the small elongated defect (Step S3ba), the defect judgement device 7 judges that the defect is not the fatal defect (Step S3c); otherwise the defect judgement device 7 judges that the defect is the fatal defect (Step S3d). A small elongated defect which is not fatal, such as a grain pattern, is a small defect having an area of several pixels.

In Step S3b, whether the defect is the elongated defect or not may be judged, for example, by $$Ge<G1 \quad (2)$$

where G1 is a predetermined value which is set by a user based on a sample test. In Step S3ba, whether the defect is the large elongated defect or not may be judged depending on the area S.

The predetermined value G1 is set, for example, at 0.5. The defect judgement device 7 judges that the defect A shown in FIG. 3 which does not satisfy Expression (2) is not the elongated defect but the fatal defect. On the other hand, the defect judgement device 7 judges that the defect B shown in FIG. 4 which satisfies Expression (2) is the elongated defect, and then examines the area S. If the area S is less than a predetermined value, the defect judgement device 7 judges that the defect is not the fatal defect.

The scratches are not only in the shape of a continuous line but also in the shape of a dotted line.

Figure 8:
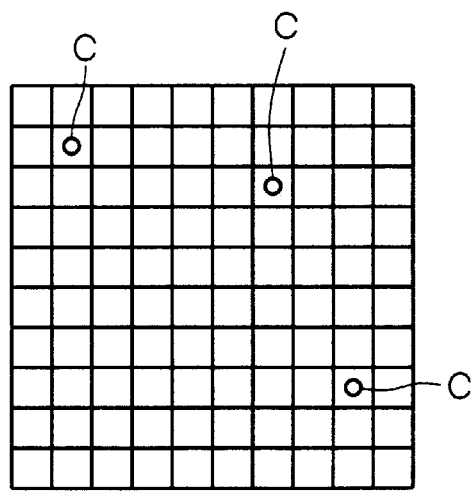
FIGS. 8 and 9 show examples of the surface information according to the third preferred embodiment.
Figure 9:
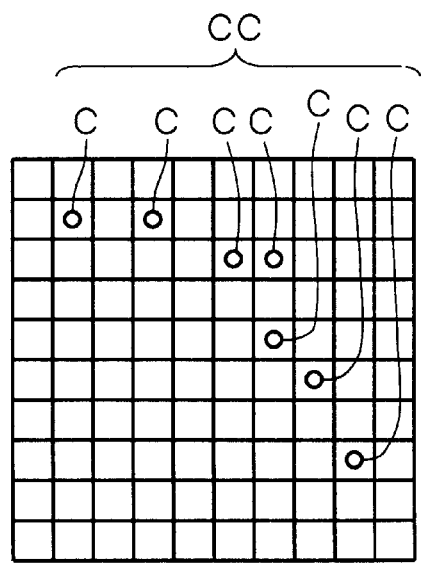

For instance, a plurality of defects C distant from each other as shown in FIG. 8 may be regarded as being independent of each other. On the other hand, a plurality of defects C close to each other as shown in FIG. 9 may be regarded as constituting a single dotted scratch.

Thus, the defect judgement device 7 takes into consideration scratches in the shape of a dotted line before Step S3b to regard a plurality of defects C close to each other, if any, as a single defect (Step S3a; clustering process). The clustering process is described below using a specific example.

The defect judgement device 7 selects a defect C and detects a second defect C present within a predetermined distance (e.g., 2 pixel blocks) from the selected defect C. If the second defect C is present, the defect judgement device 7 then detects a third defect C present within the predetermined distance from the second defect C. The defect judgement device 7 repeats the above-mentioned operation to regard the plurality of defects C close to each other as shown in FIG. 9 as a single defect CC (Step S3a). The defect CC shown in FIG. 9 wherein S=7, X=8 and Y=9 has an elongation factor Ge of about 0.062. Then, the defect judgement device 7 judges that the defect CC of FIG. 9 which satisfies Expression (2) is the large elongated defect and accordingly is the fatal defect (Step S3c).

An elongated small defect flag is set to the defect judged to be too small to be the fatal defect in Step S3c.

In this manner, if the area S of the elongated defect is greater than the predetermined value, the elongated defect is judged to be the fatal defect; otherwise, the elongated defect is not judged to be the fatal defect.

A particle defect flag is set to the defect judged to be the fatal defect in Step S3d.

The elongated defects are described above.

(Minimum Defect)

The defect in the surface foreign matter deposition mode Pa (Ps>Is) is regarded as a pattern-destroying fatal defect having a height (a dimension (measured in the Z direction) perpendicular to the X-Y plane shown in FIGS. 3 and 4), and has a high possibility of becoming the fatal defect.

On the other hand, the defect in the pattern defect mode Pd is regarded as a recessed small scratch, and has a low possibility of becoming the fatal defect.

The defect judgement device 7 makes a comparison between the detected sizes Ps and Is of the same defect (Step S3g). If the size Ps is greater than the size Is, the defect judgement device 7 judges that the defect is the fatal defect (Step S3h). If the size Ps is smaller than the size Is, the defect judgement device 7 judges that the defect is not the fatal defect (Step S3i).

However, if the size Ps greater than the size Is is extremely small, the defect is regarded as a less tall stepped defect or a stain-type defect which has a low possibility of becoming the fatal defect.

The defect judgement device 7 compares the size Ps with a predetermined value (Step S3e) before Step S3g. If the size Ps is smaller than the predetermined value, the defect judgement device 7 judges that the defect is not the fatal defect (Step S3f).

A recessed defect flag is set to the defect judged not to be the fatal defect in Step S3i.

A short stepped/stain-type defect flag is set to the defect judged not to be the fatal defect in Step S3f.

A pattern-destroying defect flag is set to the defect judged to be the fatal defect in Step S3h.

The minimum defects are described hereinabove.

Finally, the defect judgement device 7 counts the number of defects for each flag to display or output the counts, for example, to the display device 8 or to output the defects judged to be the fatal defects to the database DB (Step S3j).

As described above, the defect judgement device 7 automatically distinguishes the pieces of defect information regarding the respective defects judged not to be the fatal defects in Steps S3c, S3f, S3i from other pieces of defect information (i.e., the pieces of defect information regarding the respective defects judged to be the fatal defects in Steps S3d and S3h). This allows, for example, a process manager to know the presence or absence of the fatal defects immediately after the inspection apparatus inspects the semiconductor wafer 2. Since the degree of fatal defects is indicated by the number of fatal defects, not only the manager but also a process monitor that manages the manufacturing process can recognize the occurrence of a cause of yield reduction. Hence, the process monitor can automatically inform, for example, the process manager about the occurrence of yield reduction, thereby suppressing the yield reduction quickly. Additionally, which apparatus in a manufacturing line affects the yield is judged from the shape and size characteristics of the detected defects. This judgement is automatically made in the computer CP, and a system such that an alarm alerts the user to anomalies may be constructed.

Fourth Preferred Embodiment

A high-sensitivity inspection of a film of the type having poor surface morphology, such as a heat-treated aluminum film, for defects detects numerous defects, for example, thousands of to tens of thousands of defects. However, almost all of the numerous defects are grain patterns classified as the small elongated defects, and there are a very few fatal defects hidden in the numerous grain patterns in some cases. In such a case, since it is impossible to make a distinction between the numerous grain patterns and the very few hidden fatal defects by the number of detected defects and the size thereof, the manager observes the film to judge whether the defects are grain patterns or fatal defects. However, the manager encounters a limit when making the judgement on the numerous defects within a predetermined length of time, and the limit is at most hundreds of detected defects. If in excess of thousands of defects are detected, the manager often misses the fatal defects hidden in the grain patterns, and it is very difficult to grasp an overview of all defects within a predetermined length of time.

To solve the problem, the defect judgement device 7 in accordance with a fourth aspect of the present invention judges whether or not a defect is the grain pattern when the surface of the semiconductor wafer 2 includes a metal film such as a heat-treated aluminum film.

Figure 10:
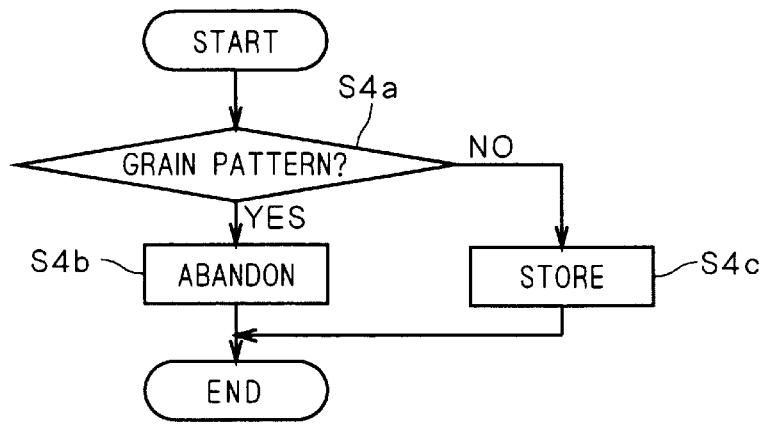
FIGS. 10 and 11 are flowcharts showing the operation of the inspection apparatus for foreign matter and pattern defects according to a fourth preferred embodiment of the present invention.

FIG. 10 is a flowchart showing the operation of the inspection apparatus according to the fourth preferred embodiment of the present invention.

The defect judgement device 7 judges whether or not the defects are the grain patterns (Step S4a). The defect judgement device 7 abandons, or excludes from the subjects of analysis, the pieces of defect information regarding the respective defects judged to be the grain patterns among those detected by the microscope illumination optical system D1 and the laser scattering type optical system D2 (Step S4b). The defect judgement device 7 stores the pieces of defect information regarding the respective defects judged not to be the grain patterns (Step S4c).

The exclusion of the pieces of defect information regarding the grain patterns among the numerous pieces of defect information from the subjects of analysis as above described greatly reduces the number of pieces of defect information to accomplish accordingly accurate analysis.

In Step S4a, whether the defects are the grain patterns or not is judged, for example, by $$Ge < G2 \tag{3}$$

where G2 is a predetermined upper limit value which is empirically set by the user based on a sample test.

The predetermined upper limit value G2 is set, for example, at 0.2. The defect judgement device 7 judges that the defect A shown in FIG. 3 which does not satisfy Expression (3) is not elongated and accordingly is not the grain pattern. On the other hand, the defect judgement device 7 judges that the defect B shown in FIG. 4 which satisfies Expression (3) is elongated and accordingly is the grain pattern.

Alternatively, whether the defects are the grain patterns or not is judged, for example, by $$G3 < Ge < G2 \tag{4}$$

where G3 is a predetermined lower limit value which is empirically set by the user based on a sample test.

The predetermined upper and lower limit values G2 and G3 are set, for example, at 0.2 and 0.1, respectively. The defect judgement device 7 judges that the defect B shown in FIG. 4 which satisfies Expression (4) is elongated and accordingly is the grain pattern.

The defects detected by the laser scattering type optical system D2 have a higher possibility of being the grain patterns than the defects detected by the microscope illumination optical system D1. Therefore, the defects to be subjected to the judgement as to whether or not they are the grain patterns may be preferably limited to those detected by the laser scattering type optical system D2 in Step S4a. This increases the accuracy of the judgement as to whether or not the defects are the grain patterns.

It cannot be denied that the defect judged to be the grain pattern from the elongation factor Ge but having a very large size has the possibility of being the pattern-destroying fatal defect. Therefore, the size of the defect is preferably compared with a predetermined value in Step S4a, and the defect is judged not to be the grain pattern if the size of the defect is greater than the predetermined value.

Figure 11:
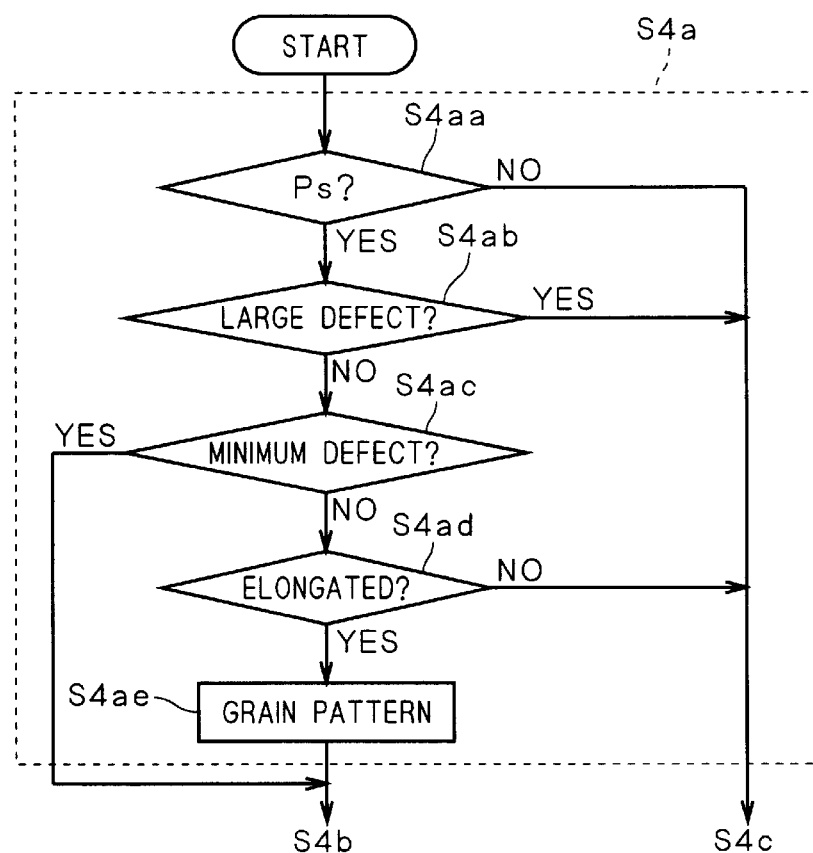

In view of the above considerations, an example of Step S4a is shown in FIG. 11. First, the defect judgement device 7 extracts a defect detected by the laser scattering type optical system D2 among the defects detected by the microscope illumination optical system D1 and the laser scattering type optical system D2 (Step S4aa).

Next, the defect judgement device 7 compares the size Ps detected by the laser scattering type optical system D2 with a predetermined value (e.g., 0.5 μm) (Step S4ab). If the size Ps exceeds the width of wiring (e.g., 0.5 μm), the defect judgement device 7 judges that the defect is not the grain pattern and stores the piece of defect information regarding the defect (Step S4c).

If the size Ps is extremely small, the defect is regarded as a less tall stepped defect or a stain-type defect which has a low possibility of becoming the fatal defect, as in Step S3e of FIG. 7. Then, the defect judgement device 7 compares the size Ps with a predetermined value (e.g., 0.1 μm) (Step S4ac). If the size Ps is less than 0.1 μm, the defect judgement device 7 abandons the piece of defect information regarding the defect (Step S4b).

Thus, the defect judgement device 7 extracts the defect having a size which falls within a predetermined range (e.g., from 0.1 μm to 0.5 μm) in Steps S4ab and S4ac.

Next, the defect judgement device 7 judges whether or not the defect having the size which falls within the predetermined range is the grain pattern (Step S4ad). This judgement may be made, for example, in a manner described with respect to Step S4a of FIG. 10. The defect judgement device 7 abandons the piece of defect information regarding the defect (Step S4b) if the defect is judged to be the grain pattern (Step S4ae), and stores the piece of defect information regarding the defect (Step S4c) if the defect is not judged to be the grain pattern.

As described above, the defect judgement device 7 judges whether or not the defects are the grain patterns in consideration for the elongation factor Ge and size thereof as shown in FIG. 11, rather than only from the elongation factor Ge as described with respect to Step S4a of FIG. 10. This increases the accuracy of abandonment of the pieces of defect information regarding the grain patterns among the numerous pieces of defect information.

Modification

According to the present invention, the inspection apparatus may be constructed such that at least the optical portion D detects the surface of the semiconductor wafer 2 in the form of a piece of surface information, and the analyzer AN detects pieces of defect information each containing the horizontal dimension, the vertical dimension and the area of a defect from the piece of surface information, thereby calculating the elongation factor of the defect from the horizontal dimension, the vertical dimension and the area thereof. Thus, either the microscope illumination optical system D1 and the signal processor 61 or the laser scattering type optical system D2 and the signal processor 62 may be dispensed with.

While the invention has been described in detail, the foregoing description is in all aspects illustrative and not restrictive. It is understood that numerous other modifications and variations can be devised without departing from the scope of the invention.

What is claimed is:

1. An apparatus for inspecting a semiconductor wafer surface for defects and foreign matter, said apparatus comprising:

an optical portion for detecting said semiconductor wafer surface in the form of a piece of surface information; and an analyzer for detecting a plurality of pieces of defect/foreign matter information each including a horizontal dimension, a vertical dimension and the area of a defect/foreign matter from said piece of surface information to calculate a predetermined elongation factor indicating a degree to which each defect/foreign matter is elongate from said horizontal dimension, said vertical dimension and said area thereof.

2. The apparatus according to claim 1, wherein said elongation factor equals said area divided by the sum of said horizontal dimension squared and said vertical dimension squared; and wherein said analyzer discriminates pieces of defect/foreign matter information including said elongation factor of less than 0.5 and pieces of defect/foreign matter information including said area of less than a predetermined value from other pieces of defect/foreign matter information.

3. The apparatus according to claim 2, wherein said analyzer excludes pieces of defect/foreign matter information detected by said analyzer and including said elongation factor of less than a predetermined value from subjects of analysis when said semiconductor wafer surface includes a metal film.

4. The apparatus according to claim 1, wherein said analyzer excludes pieces of defect/foreign matter information detected by said analyzer and including said elongation factor of less than a predetermined value from subjects of analysis when said semiconductor wafer surface includes a metal film.

5. The apparatus according to claim 1, wherein said optical portion and said analyzer operate in parallel with each other.

* * * * *